(12) United States Patent
Kashif et al.

(10) Patent No.: US 8,366,627 B2
(45) Date of Patent: Feb. 5, 2013

(54) SYSTEMS, DEVICES AND METHODS FOR NONINVASIVE OR MINIMALLY-INVASIVE ESTIMATION OF INTRACRANIAL PRESSURE AND CEREBROVASCULAR AUTOREGULATION

(75) Inventors: Faisal Mahmood Kashif, Cambridge, MA (US); Thomas Heldt, Cambridge, MA (US); George Cheeran Verghese, Newton, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 699 days.

(21) Appl. No.: 12/555,713

(22) Filed: Sep. 8, 2009

(65) Prior Publication Data
US 2010/0063405 A1    Mar. 11, 2010

Related U.S. Application Data

(60) Provisional application No. 61/095,892, filed on Sep. 10, 2008.

(51) Int. Cl.
 *A61B 5/02* (2006.01)
 *A61B 5/00* (2006.01)
(52) U.S. Cl. .................... 600/485; 600/481; 600/561
(58) Field of Classification Search .......... 600/485–486, 600/544, 561
See application file for complete search history.

(56) References Cited

U.S. PATENT DOCUMENTS
| | | | |
|---|---|---|---|
| 6,129,682 A | 10/2000 | Borchert et al. | |
| 6,589,189 B2 | 7/2003 | Meyerson et al. | |
| 6,875,176 B2 * | 4/2005 | Mourad et al. ............. | 600/442 |

FOREIGN PATENT DOCUMENTS
| | | |
|---|---|---|
| WO | WO-0243564 A2 | 6/2002 |
| WO | WO-03099131 A1 | 12/2003 |
| WO | WO-2007117570 A2 | 10/2007 |

OTHER PUBLICATIONS

International Preliminary Report on Patentability and Written Opinion dated Mar. 24, 2011 in International Application No. PCT/US2009/056270.
"Experimental Studies of the Mode of Action of Electroconvulsive Therapy," ed. by Jan-Otto Ottosson, Copenhagan, 1960.
Bono et al., "Bilateral transverse sinus stenosis predicst IIH without papilledema in patients with migraine," Neurology 2006; vol. 67, pp. 419-423.
Circulation. "Heart Disease and Stroke Statistics—2009 Update, A Report from the American Heart Association Statistics Committee and Stroke Statistics Subcommittee," Circulation, 2009; 119:e1-e161. Downloaded from circ.ahajournals.org at Mass. Inst. Technology on Mar. 18, 2010.

(Continued)

*Primary Examiner* — Patricia Mallari
*Assistant Examiner* — Tiffany Weston
(74) *Attorney, Agent, or Firm* — Ropes & Gray LLP

(57) ABSTRACT

The systems, devices, and methods described herein provide for the estimation and monitoring of cerebrovascular system properties and intracranial pressure (ICP) from one or more measurements or measured signals. These measured signals may include central or peripheral arterial blood pressure (ABP), and cerebral blood flow (CBF) or cerebral blood flow velocity (CBFV). The measured signals may be acquired noninvasively or minimally-invasively. The measured signals may be used to estimate parameters and variables of a computational model that is representative of the physiological relationships among the cerebral flows and pressures. The computational model may include at least one resistive element, at least one compliance element, and a representation of ICP.

30 Claims, 8 Drawing Sheets

OTHER PUBLICATIONS duPlessia, A.J., "Cerebrovascular Injury in Premature Infants: Current Understanding and Challenges for Future Prevention," Clin. Perinatol., vol. 35 2008, pp. 609-641.

Hayashi et al., "Plateau Wave Phenomenon (I) Correlation Between the Appearance of Plateau Waves and CSF Circulation in Patients with Intracranial Hypertension," Brain (1991), vol. 114, pp. 2681-2691.

Hayashi et al., "Plateau Wave Phenomenon (II) Occurrence of Brain Herniation in Patients With and Without Plateau Waves," Brain (1991), vol. 114, pp. 2693-2699.

Hoge et al., "Mild Traumatic Brain Injury in U.S. Soldiers Returning from Iraq," The N.E. Journal of Medicine, Jan. 31, 2008, vol. 358, No. 5, pp. 453-463.

International Search Report and Written Opinion dated Dec. 28, 2009 from International Application No. PCT/US2009/056270 filed Sep. 8, 2009.

Kashif et al., "Model-Based Estimation of Intracranial Pressure and Cerebrovascular Autoregulation," Computers in Cardiology, 2008, vol. 35, pp. 369-372.

Marmarou et al., "A nonlinear analysis of the cerebrospinal fluid system and intracranial pressure dynamics," J. Neurosurg, vol. 48, Mar. 1978, pp. 332-344.

Miller et al., "Significance of intracranial hypertension in severe head injury," J. Neurosurg., vol. 47, Oct. 1977, pp. 503-516.

Payne et al, "A Model of the Interaction between Autoregularion and Neural Activation of the Brain," Mathematical Biosciences, Elsevier, vol. 204, No. 2, Dec. 1, 2006, pp. 260-281.

Ragauskas et al., "Non-invasive Technology for Monitoring of Intracranial Volumetric Pulse Waves and Trends," Electronics and Electrical Engineering, No. 6(86), 2008, pp. 51-54.

Raksin, et al., Noninvasive intracranial compliance and pressure based on dynamic magnetic resonance imaging of blood flow and cerebrospinal fluid flow: review of principles, implementation, and other noninvasive approaches. Neurosurg. Focus, vol. 14(4): Article 4, 2003, pp. 1-8.

Rao et al., "Identification of continuous-time systems," IEEE Proc.— Control Theory Appl., Vo.. 153, No. 2, Mar. 2006.

Reid et al., "Mean intracranial pressure monitoring by a non-invasive audiological technique: a pilot study," Journal of Neurology, Neurosurgery, and Psychiatry, 1989, vol. 52:610-612. Retrieved from jnnp.bmj.com on Mar. 18, 2010.

Saljo et al., "Low-Level Blasts Raise Intracranial Pressure and Impair Cognitive Function in Rats," Journal of Neurotrauma, Aug. 2009, vol. 26, pp. 1345-1352.

Schmidt et al., "Adaptive Noninvasive Assessment of Intracranial Pressure and Cerebral Autoregulation," Stroke, Jan. 2003, p. 84-89.

Stevens et al., "A Model for Idiopathic Intracranial Hypertension and Associated Pathological ICP Wave-Forms," IEEE Trans. on Biomedical Eng., vol. 55, No. 2, Feb. 2008, pp. 388-398.

Torbey et al., "Utility of CSF pressure monitoring to identify idiopathic intracranial hypertension without papilledema in patients with chronic daily headache," Cephalalgia, 2003, vol. 24, pp. 495-502.

Ursino et al., "A simple mathematical model of the interaction between intracranial pressure and cerebral hemodynamics," J. Appl. Physiol., Nol. 82, pp. 1256-1269, 1997.

Ursino et al., "Interaction among autoregulation, CO2 reactivity, and intracranial pressure: a mathematical model," The American Physiological Society, 1998, pp. H1715-H1728.

Ursino, M., "A Mathematical Study of Human Intracranial Hydrodynamics Part 1—The Cerebrospinal Fluid Pulse Pressure," Annals of Biomedical Engineering, vol. 16, pp. 379-401, 1988.

Ursino, Mo., "A Mathematical Study of Human Intracranial Hydrodynamics Part 2—Simulation of Clinical Tests," Annals of Biomedical Engineering, vol. 16, pp. 403-416, 1988.

vandeBor et al., "Cerebral Blood Flow Velocity Regulation in Preterm Infants," Biol. Neonate, 1991, vol. 59, pp. 329-335.

Wakeland et al., "A review of physiological simulation models of intracranial pressure dynamics," Computers in Biology and Medicine, vol. 38, 2008, pp. 1024-1041.

Wakeland et al., "Assessing the prediction potential of an in silico computer model of intracranial pressure dynamics," Crit Care Med, 2009, vol. 37, No. 3, pp. 1079-1089.

Trafton, A., "Sensing when the brain is under pressure." MIT News Office (Apr. 11, 2012).

Kashif et al., "Model-Based Noninvasive Estimation of Intracranial Pressure from Cerebral Blood Flow Velocity and Arterial Pressure." Science Translational Medicine, 4:1294a44, pp. 1-9 (Apr. 11, 2012).

Goldstein, et. al., "From Lundberg to SIM-ICP: Computational Physiology and Modeling Intracranial Pressure." Science Translational Medicine, 4:129fs6, pp. 1-3 (Apr. 11, 2012).

Chacón et al., "Non-invasive Intracranial Pressure Estimation Using Support Vector Machine," 32nd Annual International Conference of the IEEE EMBS, Buenos Argentina (Aug. 31-Sep. 4, 2010).

Kimberly et al., "Brief Report Correlation of Optic Nerve Sheath Diameter with Direct Measurement of Intracranial Pressure," Academic Emergency Medicine 2008, 15:201-204.

Popovic et al., "Noninvasive Monitoring of Intracranial Pressure," Recent Patents on Biomedical Engineering, 2:3, pp. 165-179 (2009).

Ragauskas et al., "Clinical assessment of noninvasive intracranial pressure absolute value measurement method," Neurology 78, pp. 1684-1692 (May 22, 2012).

\* cited by examiner

SYSTEMS, DEVICES AND METHODS FOR NONINVASIVE OR MINIMALLY-INVASIVE ESTIMATION OF INTRACRANIAL PRESSURE AND CEREBROVASCULAR AUTOREGULATION

CROSS-REFERENCE TO RELATED APPLICATIONS

This application claims priority to U.S. Provisional Patent Application No. 61/095,892, filed Sep. 10, 2008, the contents of which are incorporated herein by reference in their entirety.

GOVERNMENT CONTRACT

This invention was made with government support under grant number 5-R01-EB001659-05 awarded by the National Institutes of Health. The government has certain rights in this invention.

BACKGROUND

The invention relates to the field of systems, devices and methods for noninvasive or minimally-invasive estimation of cerebrovascular parameters and variables. More particularly, this invention relates to the field of systems, devices, and methods for estimating intracranial pressure (ICP), cerebrovascular resistance, cerebrovascular compliance, and cerebrovascular autoregulation.

Stroke and traumatic brain injury (TBI) rank among the top healthcare challenges faced today. About 800,000 Americans suffer a new or recurrent stroke each year, and strokes take 140,000 lives in the U.S. annually, making stroke the number three cause of death in the U.S., behind only heart disease and cancer [1]. (Reference numerals listed in square brackets in this application refer to citations appearing at the end of the detailed description.) Annually, about 420,000 Americans suffer a traumatic injury to the head, and about 50,000 deaths are attributed to such injuries each year; about 6 million Americans, or 2% of the US population, live with the effects of TBI [2]. Attention to traumatic head injuries has increased recently, as about 15-28% of U.S. soldiers returning from Iraq report some degree of head injury that resulted in either loss of consciousness or altered mental status [3,4]. Recent evidence in animal models suggests that even low-level blast injuries raise ICP and impair cognitive function [5]. This is an important finding, as the majority of service-men and women reporting brain injury suffer from mild traumatic brain injury, in which ICP is currently not monitored [4].

Brain tissue is highly vulnerable to unbalanced oxygen supply and demand. A few seconds of oxygen deficit may trigger neurological symptoms, and sustained oxygen deprivation over a few minutes results in severe and often irreversible brain damage. Normally, brain tissue is protected from injury by its exquisite ability to modulate cerebral blood flow to match oxygen demand, primarily by modulating the resistance of the cerebrovascular bed. This autoregulatory ability, however, can be critically impaired due to brain damage (e.g., stroke or traumatic brain injury), putting such patients at great risk of serious further brain injury. The rapid dynamics coupled to the potential for severe injury necessitates continuous, and ideally non-invasive, cerebrovascular monitoring, at least in the populations at greatest risk for developing brain injury.

Monitoring the cerebrovascular state of a patient, or an animal, suffering from cerebrovascular accident or disease—such as stroke, cerebral hemorrhage, TBI or hydrocephalus—requires assessing the cerebrovascular system's ability to regulate a desired blood supply. Cerebral blood flow depends on arterial blood pressure (ABP) and ICP as well as cerebrovascular parameters, such as cerebrovascular resistance and cerebrovascular compliance. Specifically, the difference of ABP and ICP is termed cerebral perfusion pressure (CPP), and constitutes the driving pressure for cerebral blood flow. As a consequence, monitoring of ICP, cerebrovascular parameters and autoregulation is central to diagnosis, tracking of disease progression, and titration of therapy for a range of conditions involving cerebral pathophysiology.

Monitoring ICP in current clinical practice requires penetration of the skull and insertion of a catheter or pressure sensor into the ventricular or parenchymal space [24]. Thus current methods for monitoring ICP are significantly invasive, and are therefore reserved for only the most severe of cases. Other measurement methods based on lumbar puncture are also used in clinical practice; however, in addition to being invasive, these methods pose a risk of herniation of the brain stem in patients suffering from intracranial hypertension. The invasiveness of current methodologies for the measurement of ICP results in such measurements being taken only in patients at highest risk of developing intracranial hypertension and associated compromised cerebral blood flow. Thus, the current ICP monitoring paradigm excludes a large patient pool that can potentially benefit from such monitoring, such as those suffering from or suspected of suffering from mild traumatic brain injury. Therefore, there is a strong need for noninvasive or minimally-invasive methods and systems for estimating and monitoring ICP and cerebrovascular autoregulation.

Research and development efforts related to noninvasive or minimally-invasive estimation of ICP and autoregulation have been disclosed in the scientific literature and patent descriptions, particularly over the last decade [9-15]. None of these approaches, however, has all of the following desirable features: ability to estimate ICP, hence CPP; ability to estimate cerebrovascular resistance and compliance, thereby permitting an assessment of autoregulation; ability to estimate these variables and parameters continuously, at beat-to-beat temporal resolution, and in real time; minimally or non-invasively; at the patient's bedside; without reference to patient- or population-specific data; ability to exploit fundamental physiological relationships rather than empirical or statistical associations; without the need for any calibration; and at high fidelity.

Furthermore, the portion of the literature addressing cerebrovascular autoregulation has typically been handicapped by the lack of a noninvasive ICP estimate, and has therefore had to substitute ABP for CPP in assessing autoregulation. This presents a serious methodological deficiency for existing indices of autoregulation.

Non-invasive and continuous estimation of ICP will have impact at three levels. First, it will save patients from the associated risks and complications. Second, it will open up the possibility for use in many other scenarios where ICP monitoring would improve care, but is currently avoided because of the highly invasive nature of available methods. For instance, the somewhat arbitrary boundaries that presently distinguish between mild, moderate and severe TBI could perhaps be clarified [8]. Given the brain's sensitivity to even short disruptions in oxygen supply, continuous tracking of ICP and vascular autoregulatory capacity seem indicated for diagnosis and monitoring of mild TBI. Another example might be the monitoring and programming of CSF shunts in chronic hydrocephalus patients. Third, non-invasive ICP estimation could be informative in a still broader population where elevated ICP may be involved in the pathophysiological pathways, possibly even in such common conditions as migraine (where studies indicate a correlation between intracranial hypertension and migraine involving bilateral transverse sinus stenosis [27]) and chronic daily headache [28].

SUMMARY

The systems, devices, and methods described herein in various embodiments provide non-invasive, continuous, real-time estimates of intracranial pressure, cerebrovascular resistance, and cerebrovascular compliance, thus allowing an assessment of cerebrovascular autoregulation.

The systems, devices, and methods described herein include processes for estimating and monitoring cerebrovascular system properties and ICP as functions of time from one or more measurements or measured signals. These measured signals may include central or peripheral arterial blood pressure (ABP), and cerebral blood flow (CBF) or cerebral blood flow velocity (CBFV). Furthermore, these measured signals may be acquired noninvasively or minimally-invasively. As described herein, the measured signals are used in combination with a computational model that represents the physiological relationships among cerebrovascular flows and pressures. In some embodiments, the computational model includes at least one resistive element, at least one compliance element, and a representation of ICP.

The systems, devices and methods described herein could operate on minimally- or noninvasive measurements taken from a patient, e.g., cuff-based ABP measurements taken from a patient's extremity, and ultrasound-based cerebral blood flow (CBF) or cerebral blood flow velocity (CBFV) measurements taken at the level of a cerebral artery, and may provide continuous estimates, i.e., consecutive estimates, with each estimate corresponding to one cardiac cycle in a consecutive sequence (or a beat-by-beat estimate), in real-time to be displayed on the display of a patient monitor.

In one aspect, the invention relates to a method for estimating ICP, based at least in part on estimating parameters and variables of a computational model. The method includes a processor receiving ABP measurements and at least one of CBF measurements and CBFV measurements. The method further includes the processor computing an estimate of ICP based at least in part on estimating the parameters and the variables of the computational model and the received measurements. The computational model represents the physiological relationships among cerebrovascular flows and pressures and includes at least one resistive element and at least one compliance element and a representation of ICP.

In some embodiments, the processor may compute the estimates based at least in part on minimizing an error criterion such as least-squared error. In some embodiments, the processor does not receive patient-specific and/or population-specific data.

In some embodiments, the processor also computes an estimate of at least one of a cerebrovascular resistance and a cerebrovascular compliance. In some embodiments, the processor may use the estimated cerebrovascular compliance to compute an estimate of a blood flow through the cerebrovascular resistance. In some embodiments, the parameters and the variables of the computational model are computed at least once per cardiac cycle. In some embodiments, the parameters and the variables of the computational model are estimated using a data window of a pre-specified size. The size may be any suitable fraction of the length of a cardiac cycle or beat, e.g., ½ to 1/20 of a beat, or any suitable multiple of the length of a cardiac cycle, e.g., 1, 2, 3, 5, 10, 15, 20 or 30 beats.

In some embodiments, the processor computes estimates of the parameters and the variables using a two-stage algorithm. The processor may compute estimates of a cerebrovascular compliance in a first stage of the two-stage algorithm, and may compute estimates of at least one of a cerebrovascular resistance and ICP in a second stage of a two-stage algorithm.

In a second aspect, the invention relates to a method for estimating a cerebrovascular resistance based at least in part on estimating parameters and variables of a computational model. The method includes a processor receiving ABP measurements and at least one of CBF measurements and CBFV measurements. The method further includes the processor computing an estimate of the cerebrovascular resistance based at least in part on estimating the parameters and the variables of the computational model and the received measurements. The computational model represents the physiological relationships among cerebrovascular flows and pressures and includes at least one resistive element and at least one compliance element and a representation of ICP. In some embodiments, the processor also computes an estimate of at least one of ICP, a cerebrovascular compliance, and an assessment of cerebrovascular autoregulation.

In a third aspect, the invention relates to a method for estimating a cerebrovascular compliance based at least in part on estimating parameters and variables of a computational model. The method includes a processor receiving ABP measurements and at least one of CBF measurements and CBFV measurements. The method further includes the processor computing an estimate of the cerebrovascular compliance based at least in part on estimating the parameters and the variables of the computational model and the received measurements. The computational model represents the physiological relationships among cerebrovascular flows and pressures and includes at least one resistive element and at least one compliance element and a representation of ICP. In some embodiments, the processor also computes an estimate of at least one of ICP, a cerebrovascular resistance, and an assessment of cerebrovascular autoregulation.

In a fourth aspect, the invention relates to a device for estimating at least one of a cerebrovascular compliance, a cerebrovascular resistance, ICP and an assessment of cerebrovascular autoregulation, based at least in part on estimating parameters and variables of a computational model. The device includes a processor, a memory in communication with the processor, and a display in communication with the processor. The processor is configured to receive ABP measurements, receive at least one of CBF measurements and CBFV measurements, and compute an estimate of at least one of the cerebrovascular compliance, the cerebrovascular resistance, ICP and the assessment of cerebrovascular autoregulation. This estimate is computed based at least in part on estimating the parameters and the variables of the computational model and the received measurements. The computational model represents the physiological relationships among cerebrovascular flows and pressures and includes at least one resistive element and at least one compliance element and a representation of ICP. The memory is configured to store at least one of the received measurements and the computed estimate. The display is configured to display an estimate of at least one of cerebrovascular compliance, cerebrovascular resistance, ICP and cerebral autoregulation.

In some embodiments, the device further includes a sensing device in communication with the processor for sensing the ABP measurements. This sensing device may include one of an arterial catheter, a tonometry sensor, a sphygmomanometer sensor, and a photoplethysmography sensor.

In some embodiments, the device further includes a sensing device in communication with the processor for sensing at least one of the CBF measurements and the CBFV measurements. This sensing device may include an ultrasound sensor, e.g., a Doppler-based device.

In some embodiments, the device further includes a signal quality processor in communication with the processor. The signal quality processor is configured to assess the quality of the received measurements. Optionally, the signal quality processor is configured to remove unwanted portions of the received measurements. The unwanted portions may include noise and artifact.

In some embodiments, the device further includes a smoothing processor configured to filter the computed estimate. The filter may include a median filter.

In this application, embodiments will be described in reference to the estimation of one or more cerebrovascular parameters or variables using one or more computational models that represent physiological relationships among cerebrovascular flows and pressures. It is to be understood that the systems and methods discussed herein are applicable to systems, devices, and methods in which other computational models may be employed, or to applications in which the other physiological parameters or variables are estimated using computational models.

BRIEF DESCRIPTION OF THE DRAWINGS

The invention description below refers to the accompanying drawings, of which.

DETAILED DESCRIPTION

Figure 1:
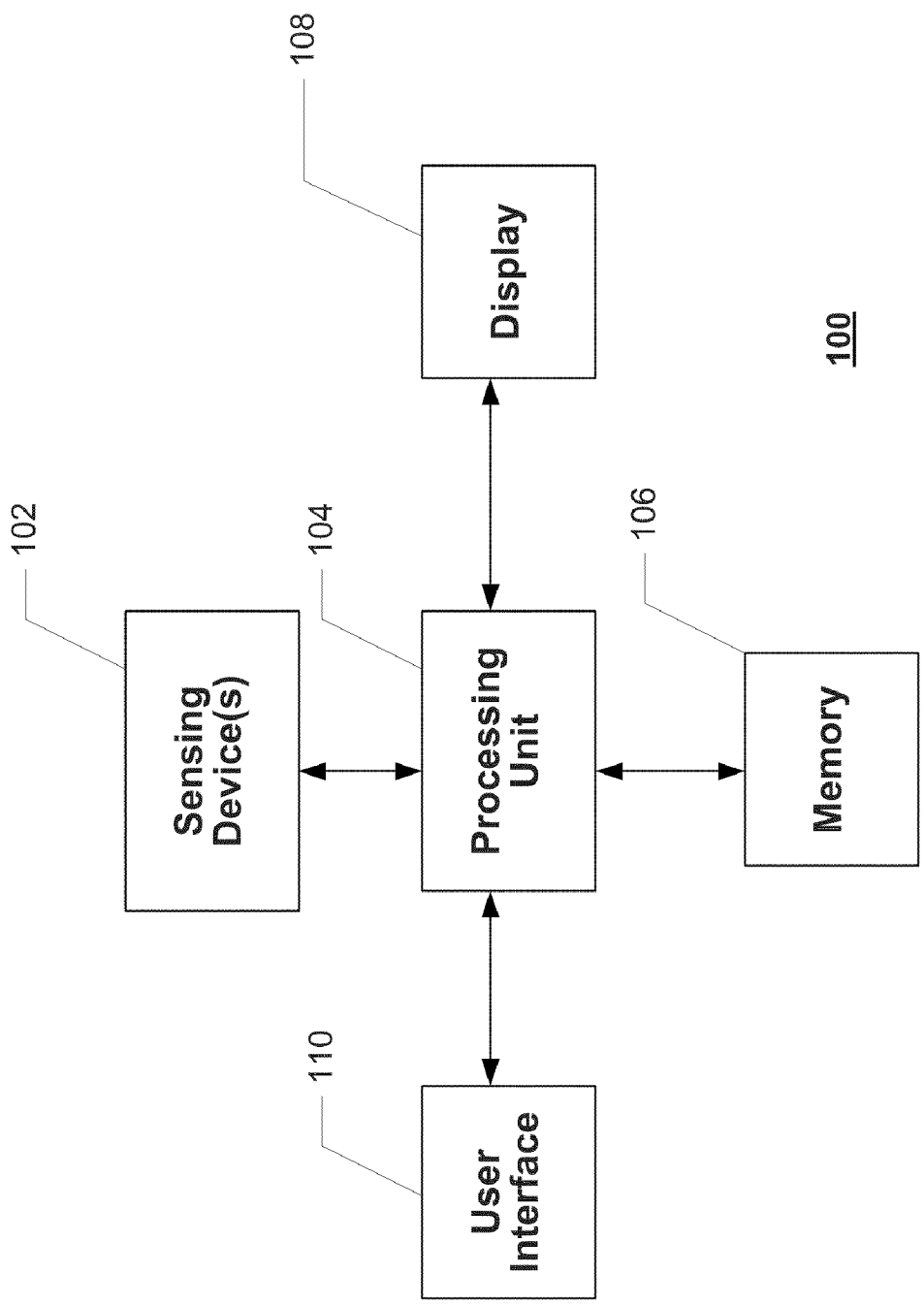
FIG. 1 is a block diagram of a medical device for estimating cerebrovascular parameters and variables, according to an illustrative embodiment.

To provide an overall understanding of the invention, certain illustrative embodiments will now be described. However, it will be understood by one of ordinary skill in the art that the methods described herein may be adapted and modified as appropriate for the application being addressed, and that the systems, devices, and methods described herein may be employed in other suitable applications, and that such other additions and modifications will not depart from the scope hereof.

Introduction

Applicants' approach is based on using a computational model of the cerebrovascular and/or intracranial dynamics, in which the model parameters have physiological relevance. Over the past few decades, several such models have been proposed and studied in the literature [17-23]. Applicants have adapted the well-established model by Ursino and Lodi [20] by making necessary modifications to represent the pulsatile nature of the variables captured in the computational model. These modifications allow for the exploitation of both the intra-beat and beat-to-beat waveform variations, as will be described further in reference to FIGS. 3 and 4.

The systems, devices, and methods described herein allow for the estimation and monitoring of cerebrovascular system properties and ICP from one or more measurements or measured signals [16]. These measured signals may include central or peripheral ABP, and CBF or CBFV. The measured signals may be acquired noninvasively or minimally-invasively. The measured signals are used in combination with a computational model that represents the physiological relationships among cerebrovascular flows and pressures. The computational model used for the estimates includes at least one resistive element, at least one compliance element, and a representation of ICP.

Applicants' approach is advantageous as Applicants represent the cerebrovascular dynamics (i.e., relationships between cerebrovascular flows and pressures) by a computational model that is compact (i.e., reduced-order or containing only a few elements), yet physiologically meaningful. In some embodiments, Applicants' approach includes an estimation algorithm that exploits the intra-beat (i.e., within each beat) and inter-beat (i.e., beat-to-beat) features of the received ABP and CBF velocity waveforms, to compute estimates of one or more parameters of the computational model. Applicants' estimation algorithm takes into account artifacts, uncertainty, and noise in the received measurements while providing beat-by-beat estimates of one or more of ICP, cerebrovascular resistance, and cerebrovascular compliance. The estimation algorithm may include one or two stages as described further in relation to FIGS. 2 and 6.

In some embodiments, a known or fixed computational model is used that requires neither any training nor learning, nor externally supplied patient-specific or population-based parameters. This computational model is generally (1) a simple, compact representation of cerebrovascular physiology, (2) obtained from a detailed physiologically based model via multi-scale analysis (i.e., time-scale separation), hence retaining the physiological interpretability of parameters and variables, and (3) represents the pulsatile nature (intra-beat dynamics) of the cerebrovascular pressures and flows. Inter alia, these features provide significant advantages as described with respect to the illustrative embodiments of FIGS. 1-8. In particular, the computational model allows for estimation of all the model parameters, instead of a single empirical relationship between a desired quantity and the measurements. In some embodiments, the intra-beat features and beat-to-beat features are extracted from the received measurements to provide, in real-time, estimates of one or more unknown quantities from the following set: ICP, cerebrovascular resistance, cerebrovascular compliance, and cerebrovascular autoregulation.

The quality of the estimates thus obtained is generally independent of the length of the measured signal or measurement signal history in a particular patient. This is because the Applicants' estimation algorithm based on the computational model does not need to learn or train on extensive patient-specific data or data from a population of patients. Furthermore, the use of a short sliding window in the Applicants' algorithm allows close tracking of the temporal variations in cerebrovascular parameters and variables.

Illustrative embodiments will now be described in reference to FIGS. 1-8.

FIG. 1 is a block diagram of a cerebrovascular parameter and variable estimation device 100, according to an illustrative embodiment. Such a device may be part of a patient monitoring system, e.g., a bed-side monitor. Device 100 includes one or more sensing devices 102, a processing unit 104, a memory 106, e.g., Read-Only Memory (ROM), a display 108, and a user interface 110. The processing unit may include one or more processors, including a signal quality processor, a computation processor, an extraction processor, and a smoothing processor. Each of these processors may be in communication with one another and with one or more of memory 106, sensing devices 102, display 108, and user interface 110. Sensing devices 102 may include one or more invasive or noninvasive devices. Memory 106 may include any form of persistent storage, e.g., a hard drive, flash memory, etc. Furthermore, memory 106 may be a local memory or a memory attached to a network accessible to the processing unit 104.

Processing unit 104 operates on measurements that are either received from sensing devices 102, or stored in memory 106. The received measurements may include ABP measurements, and CBF or CBFV measurements. Thus, sensing devices 102 may include a sensing device for measuring ABP. Such a sensing device could include a minimally-invasive arterial catheter, or a minimally-invasive or noninvasive sphygmomanometer sensor, tonometric sensor, or photoplethysmographic sensor, each of which would be configured to measure ABP. The blood pressure may be measured at any suitable central or peripheral artery in the cardiovascular system.

In clinical environments, ABP is generally measured continuously by a Finapres (Portapres, Finometer) device on the finger or by a radial-artery catheter, while CBFV is generally measured by transcranial Doppler (TCD) focused, for example, on the middle cerebral artery (MCA). Assuming that the radius or cross-sectional area of the MCA varies relatively little, the velocity can be converted into regional CBF by multiplying the mean flow by the cross-sectional area of the artery. The ABP and CBF or CBFV signals are typically sampled at a rate high enough to capture essential intra-beat morphological features of each waveform. In some embodiments, the measured arterial blood pressure may be received by processing unit 104 as samples of a continuously measured arterial blood pressure sampled at an appropriate frequency, e.g., 20 Hz-250 Hz. Generally, a sampling rate of 100 Hz or greater is used. Alternatively, or additionally, the measured arterial blood pressure may be received as discrete samples of systolic, diastolic, or mean arterial blood pressure.

Processing unit 104 operates on measurements in accordance with computer-executable instructions loaded into memory 106. The instructions will ordinarily have been loaded into the memory 106 from local persistent storage in the form of, say, a disc drive with which the memory 106 communicates. The instructions may additionally, or instead, be received by way of user interface 110. The system may also receive user input from user interface 110 via user input devices such as a keyboard, mouse, or touch-screen.

In operation, processing unit 104 computes estimates of at least one of ICP, cerebrovascular resistance, cerebrovascular compliance, and an assessment of cerebrovascular autoregulation, based at least in part on estimating the parameters and the variables of a computational model and the received measurements. The computational model is representative of the relationships among cerebrovascular flows and pressures as described in reference to FIGS. 2, 3A, and 3B, and includes at least one resistive element and at least one compliance element and a representation of ICP. The computed estimates, e.g., cerebrovascular resistance or ICP, may be displayed on display 108. The computed and displayed estimates may be relative or absolute. For instance, in some embodiments, the radius or cross-sectional area of the cerebral artery is known or estimated, and the computed estimates are thus absolute. In other embodiments, however, the radius or cross-sectional area of the cerebral artery is not known, and the computed estimates may be relative estimates, i.e., estimates that need to be scaled (by the radius or cross-sectional area of the cerebral artery, for example) in order to yield a calibrated or absolute estimate. In some embodiments, ICP is obtained without the need for scaling.

Figure 2:
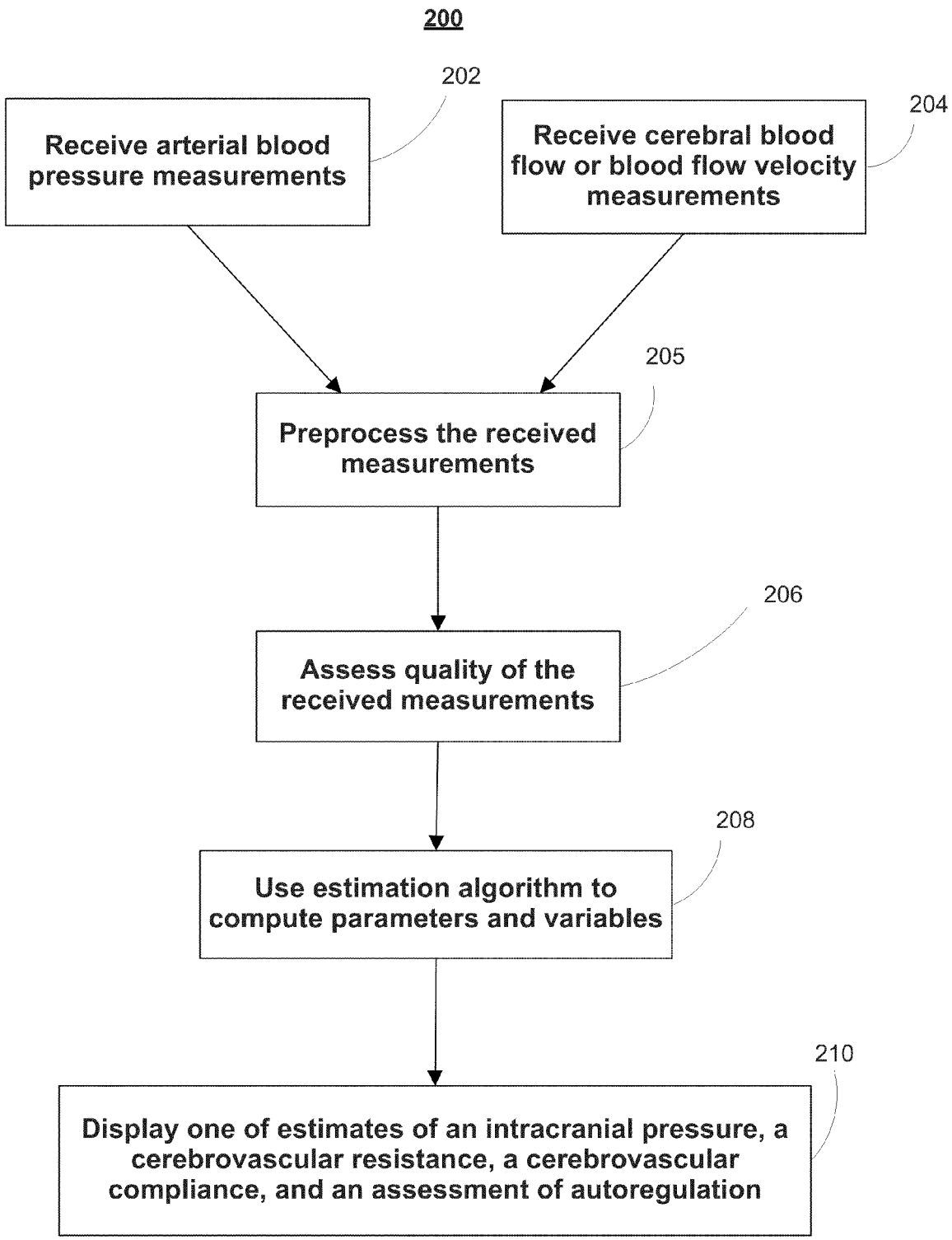
FIG. 2 is a process flow diagram of a process for estimating cerebrovascular parameters and variables, according to an illustrative embodiment.

FIG. 2 is a process flow diagram 200 including steps suitable for estimating one or more cardiovascular parameters and variables using a computational model, according to an illustrative embodiment. This process may be implemented on processing unit 104 of FIG. 1. The steps shown in FIG. 2 are only illustrative and in general may be performed in any order. In addition, some of the steps shown in FIG. 2 may be optional.

With continued reference to FIGS. 1 and 2, processing unit 104 may receive ABP measurements (202) and/or CBF or CBFV measurements (204). These measurements may be pre-processed by an extraction processor and/or a computation processor that is part of processing unit 104 (205). The signal quality of the received measurements may also be assessed by a signal quality processor that is part of processing unit 104 (206). In some embodiments, the received measurements, which may have been sampled at different rates (e.g., 20 Hz, 30 Hz, 50 Hz, or 70 Hz), may be re-sampled at a higher rate (e.g., 120-250 Hz) by the extraction processor. This re-sampling may be advantageous as it may aid the detection of the onset times and/or other intra-beat features of the ABP, CBF, or CBFV measurements. Those skilled in the art will realize that the re-sampling frequency may be any suitable frequency.

In some embodiments, to remove noise, such as electromagnetic interference (EMI) or sampling and/or quantization noise, the signal quality processor may be configured to implement a low-pass FIR filter with cut-off frequency of 0.75-40 Hz, preferably 16 Hz. Those skilled in the art will realize that this cut-off frequency may be any suitable frequency. In some embodiments, the signal quality processor may automatically assess the quality of the received ABP, CBF, and CBFV measurements by classifying the received measurements into data segments with noise, data segments with artifact, and data segments in which no measurements were recorded. These labels may be combined to form a signal quality metric for use in an estimation algorithm for a computation model as described further in reference to FIGS. 4A-6.

With continued reference to FIGS. 1 and 2, the computation processor of the processing unit 104 may use an estimation algorithm to compute parameters and variables (208) of this computational model as described further in reference to FIGS. 4A-6. Finally, the processing unit communicates with the display 108 and displays one or more of estimates of an ICP, a cerebrovascular resistance, cerebrovascular compliance, and an assessment of autoregulation (210).

The Cerebrovascular Circulation in Humans

Figure 3A:
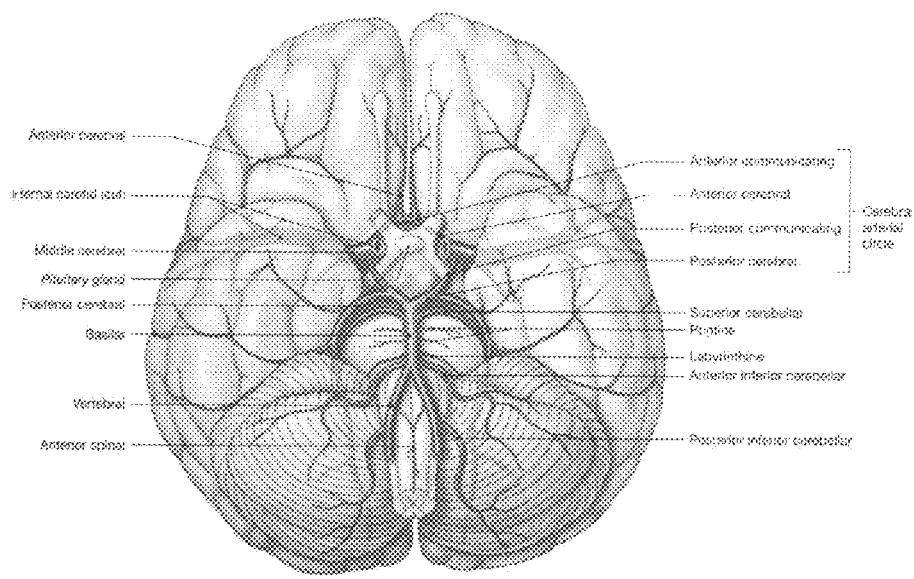
FIG. 3A illustrates cerebral circulation in humans as illustrated in Human Anatomy, Martini et al. [31]
Figure 3B:
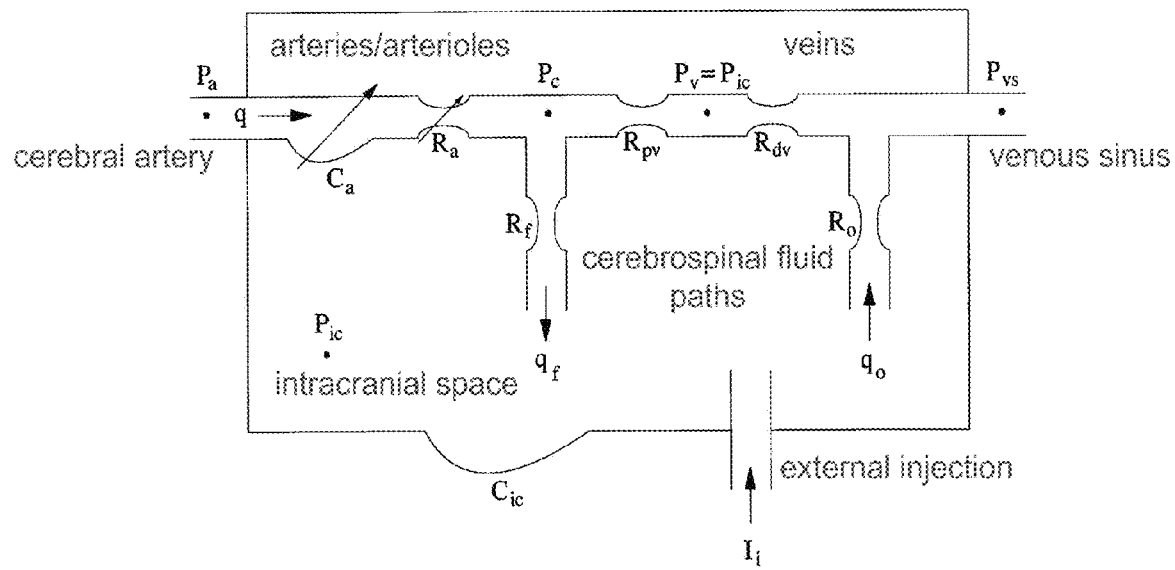
FIG. 3B illustrates a physiologic compartmental view of the intracranial space as illustrated in Ursino et al. [20]

FIG. 3A illustrates the cerebral circulation in humans as illustrated in Human Anatomy, Martini et al. [31], while FIG. 3B illustrates a physiologic compartmental view of the intracranial space as illustrated in Ursino et al. [20].

In FIGS. 3A and 3B, important blood vessels carrying blood to cerebral tissue and the path of formation and re-absorption of cerebrospinal fluid (CSF) are shown, where ICP ($p_{ic}$) indicates the CSF pressure in the cranial space. Perfusion to the brain directly depends on ABP, ICP, and the physical properties of the cerebral vasculature (resistance and compliance). For example, an asymmetry between the left and right hemispheres, as picked up from the estimates of resistance of the right and left middle cerebral artery territories, might be indicative of a unilateral stroke. There is also growing evidence suggesting that many pre-term neonates lack a fully developed cerebral vasculature and hence the ability to regulate cerebral blood supply [29-30]. Monitoring of resistance and compliance of the cerebrovascular blood vessels can prove useful in such cases.

Since venous pressure ($p_{vs}$) is typically lower than ICP, ICP establishes the downstream pressure for perfusion through the cerebral vasculature. Cerebral perfusion pressure (CPP) is thus defined as the difference between arterial blood pressure ($p_a$) and ICP. Dividing CPP by the cerebral blood flow (CBF) yields the effective resistance of the cerebral vasculature. An increase in ICP accordingly can cause a decrease in CPP and a consequent drop in CBF, if the resistance does not vary significantly. The drop in CBF can jeopardize tissue oxygenation. Second, even when CBF may not drop dangerously low due to an active autoregulation, an elevated ICP can still cause compression of the brain tissue, neural damage and ultimately brain herniation and brain death. Finally, abundant evidence suggests that sustained elevation of ICP is associated with a poor prognosis and outcome [6]. Hence, in order to track the cerebrovascular state of a patient and guide therapy, it is critical to monitor ICP.

The importance of ICP monitoring to critical care in neurological injury is well-established [8]. Medical guidelines for TBI patients, for example, require maintaining ICP below 20-25 mmHg and CPP between 50 and 70 mmHg [8]. Typical therapy for treating high ICP includes hyperventilation, head-up positioning, administration of drugs such as osmotic diuretics and corticosteroids, drainage of cerebrospinal fluid (CSF), or even surgical relief of pressure through craniectomies [8].

Normal ICP is 10-15 mmHg in adults [7]. However, in a variety of pathological conditions (cerebral edema, brain tumor, intracranial hemorrhage, hydrocephalus, sagittal sinus thrombosis, to mention a few), ICP can rise dramatically beyond these normal values. In all such conditions, compromised blood supply to the brain tissue can rapidly result in loss of neuro-cognitive function, and ultimately irreversible cerebral damage.

Figure 4A:
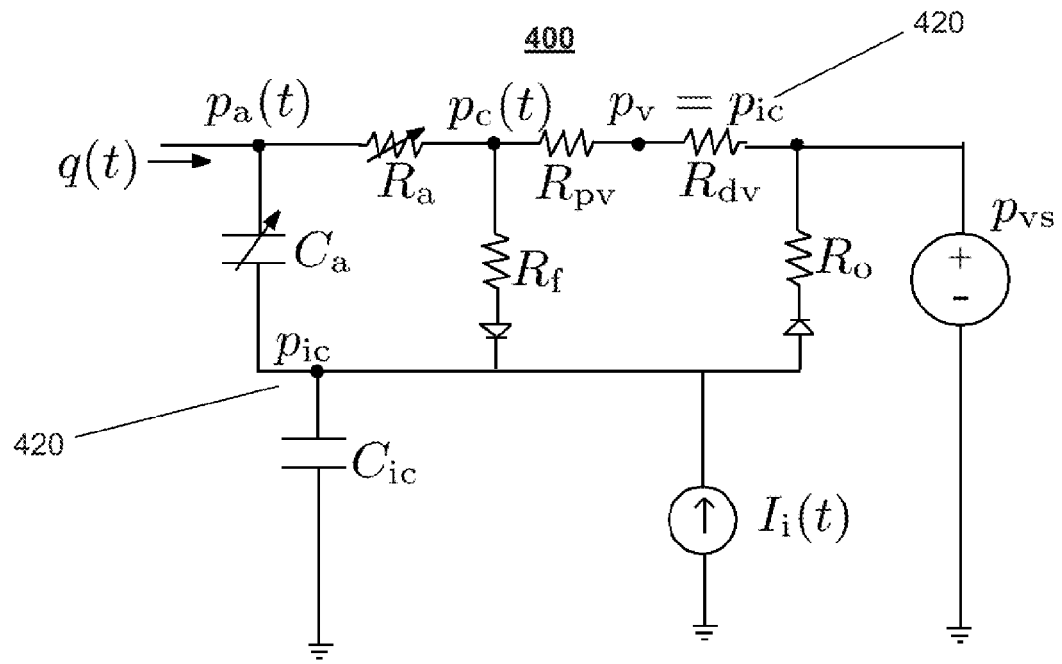
FIGS. 4A and 4B illustrate computational circuit-analog models of cerebrovascular dynamics, according to an illustrative embodiment.
Figure 4B:
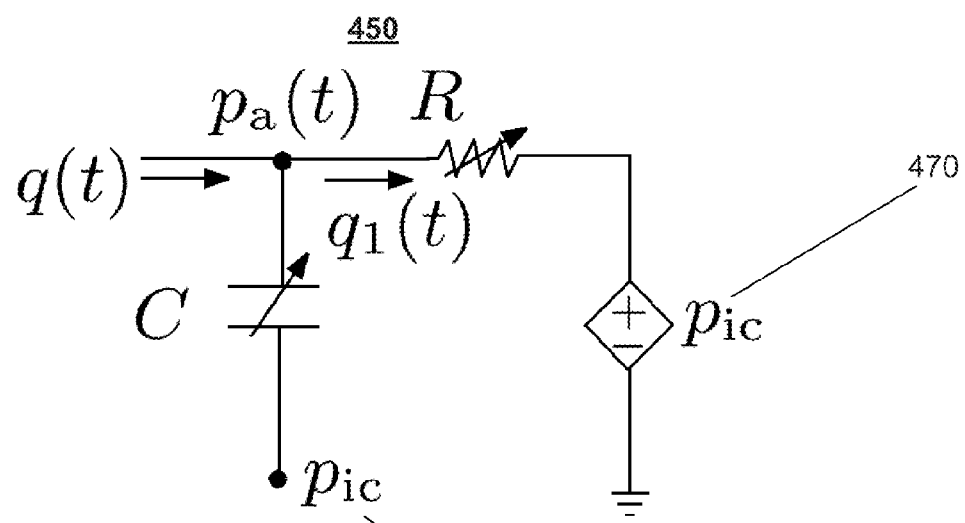
Figure 7:
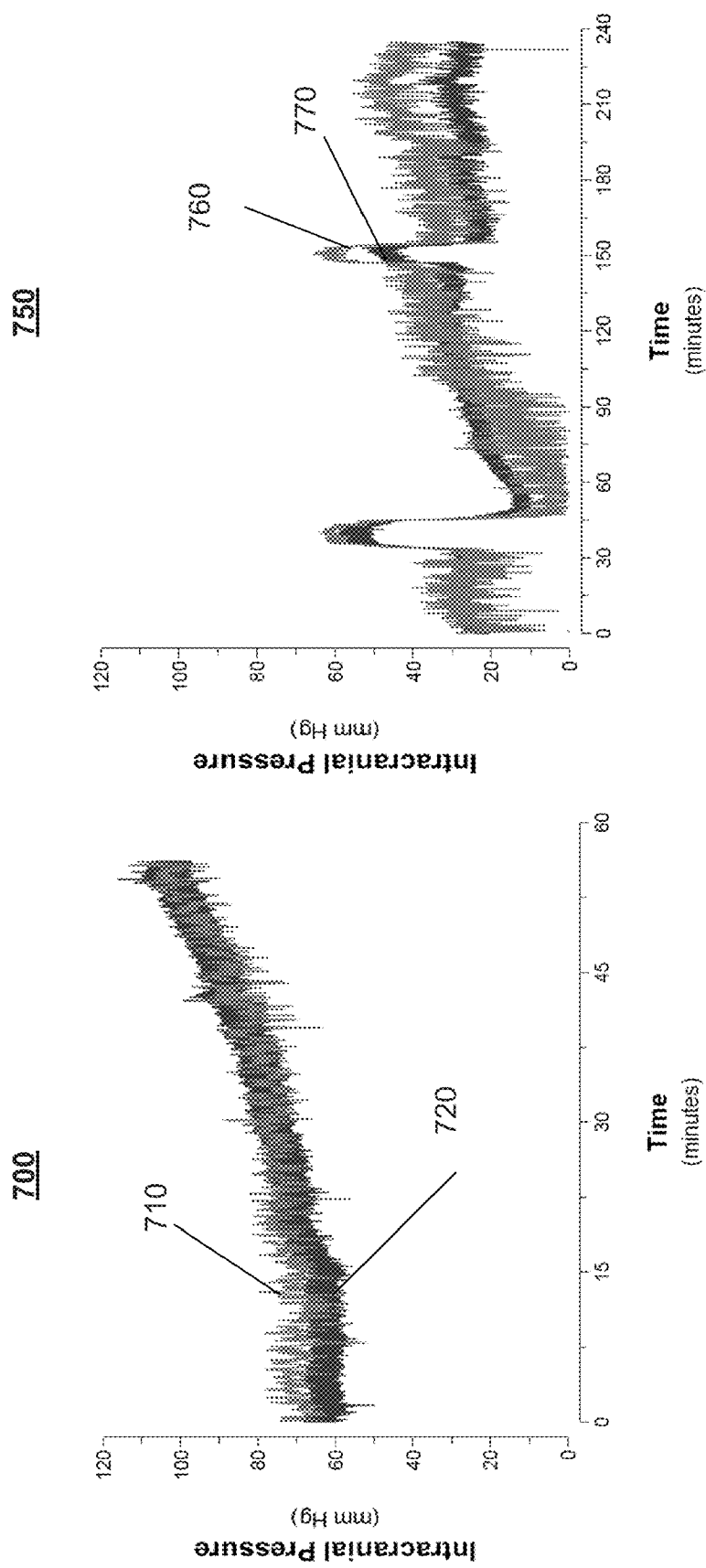
FIG. 7 illustrates comparisons of estimates of ICP with actual ICP measurements for two patients, according to an illustrative embodiment.
Figure 8:
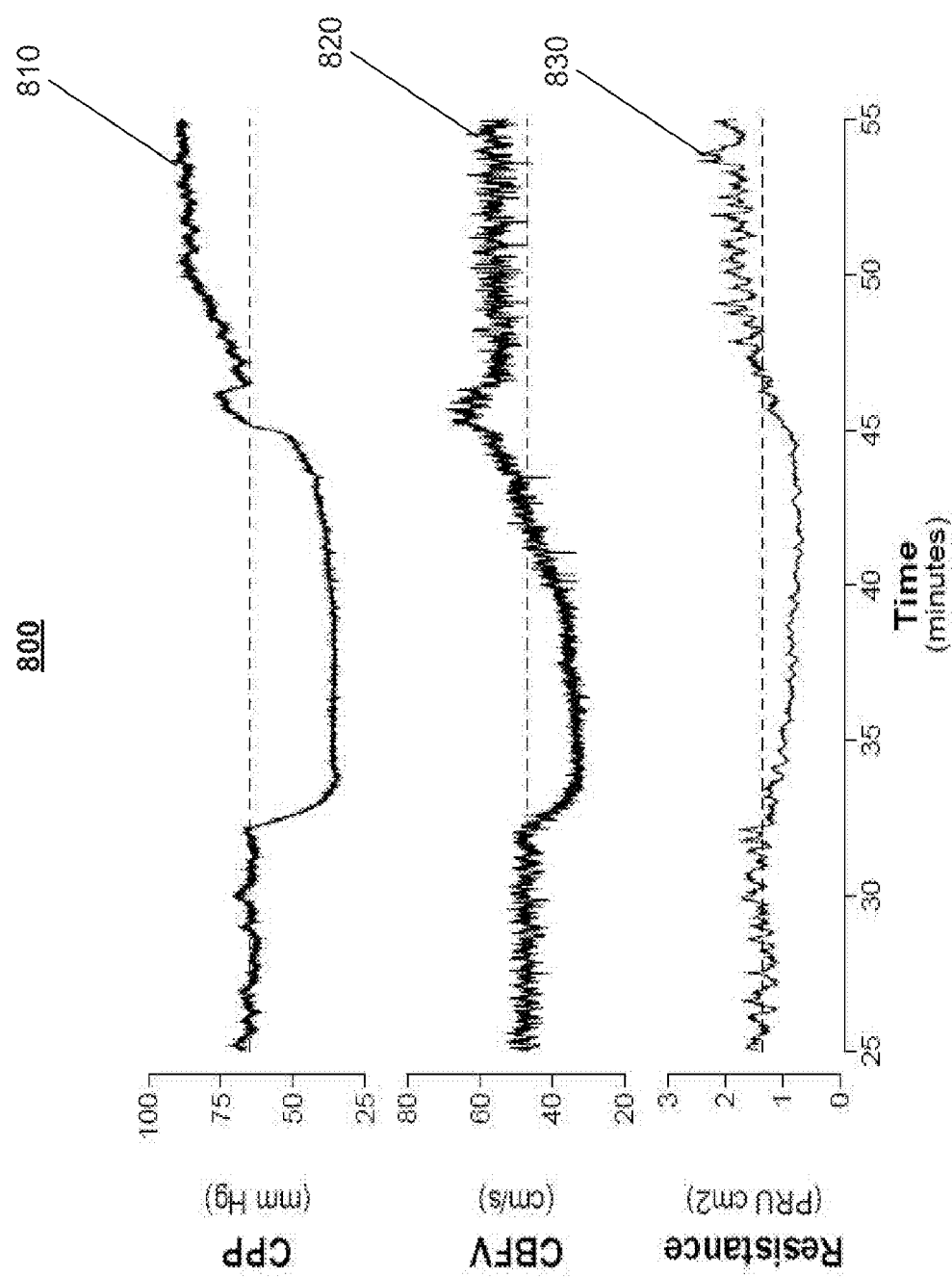
FIG. 8 illustrates the use of cerebrovascular resistance estimates along with ICP estimates to obtain an assessment of cerebrovascular autoregulation for the second patient of FIG. 7, according to an illustrative embodiment.

Applicants will now describe computational models of cerebrovascular dynamics with reference to FIGS. 4A and 4B. These models may be used with the estimation algorithm described in relation to FIG. 6 to produce estimates of parameters and variables, e.g., ICP in the computational models as shown in FIGS. 7-8.

Computational Models

FIGS. 4A and 4B illustrate computational circuit-analog models 400 and 450 of cerebrovascular dynamics, according to an illustrative embodiment. FIG. 4A shows a computational model 400 proposed by the Applicants [16] based at least in part on a well known lumped-parameter model of the cerebrovascular system first proposed by Ursino et al. [20]. Computational model 400 is relatively simple, yet captures the key dynamics of the cerebrovascular system. Computational model 400 is drawn in terms of an electrical circuit analog, in which current represents blood flow, and voltage represents pressure. The resistance to flow and compliance of the blood vessels are represented by their respective electrical analogs, resistors and capacitors. CSF formation/outflow pathways are similarly represented by resistors. The diode symbols indicate the unidirectional flows, and the current source represents any external injection of fluid into (or removed from) the intracranial space. The autoregulatory mechanism is indicated by the controlled (and time-varying) cerebrovascular compliance $C_a$ and cerebrovascular resistance $R_a$. Finally, intracranial compliance represents the capacity of the intracranial space to accommodate CSF volume, mainly due to elasticity of the brain tissue and compression of the blood vessels.

Pressure at the inlet of a main artery into the cerebral section—right or left middle cerebral artery (MCA), for example—is represented as $p_a(t)$ and is assumed to be almost the same as systemic arterial pressure. CBF is represented as the pulsatile flow input q(t) to the computational model 400. In some embodiments, CBFV may be used as an input to the computational model 400 instead of, or in addition to, CBF q(t). The arterial-arteriolar segment is represented by a single cerebrovascular compliance, $C_a$, mainly due to large arteries, and a single cerebrovascular resistance, $R_a$, for both large and small arteries and arterioles. Hence, the cerebrovascular resistance and cerebrovascular compliance are "lumped-parameters" of the computational model. Both $C_a$ and $R_a$ are modeled as slowly time-varying computational model parameters that can be used to assess cerebrovascular autoregulation. ICP, labeled as $p_{ic}(t)$ in model 400, acts as the downstream pressure for the flow path, a consequence of the Starling resistor mechanism causing the cerebral veins to collapse in the region where ICP exceeds venous pressure. In terms of parameter estimation using computational model 400, the systems, devices, and methods disclosed herein allow for the estimation of one or more of ICP 420 ($p_{ic}(t)$), cerebrovascular resistance $R_a$, and cerebrovascular compliance $C_a$, using measurements of the ABP signal $p_a(t)$ and the CBF signal q(t).

In the computational model 400 of FIG. 4A, the venous space is divided into two cerebrovascular resistances, $R_{pv}$ and $R_{dv}$, respectively, to distinguish proximal veins from the collapsible lateral lacunae and bridge veins. The computational model 400 assumes that the last section of the venous system is collapsed and that therefore cerebral venous pressure is almost equal to the pressure external to the veins, namely ICP, i.e., $p_v=p_{ic}$. Furthermore, the resistances $R_{pv}$ and $R_{dv}$ are kept constant since they play no role in autoregulation. Venous compliance is ignored in the computational model 400. Pressure at the venous sinus is denoted as constant $p_{vs}$. CSF formation occurs at the capillaries and is captured by a unidirectional flow with a high resistance $R_f$, while CSF reabsorption or outflow is represented by a cerebrovascular resistance $R^o$ at the level of large veins. $R_o$ is also large compared to $R_a$. ICP is denoted by $p_{ic}(t)$ 420 and the cerebrovascular compliance of the intracranial space is denoted as $C_{ic}$. This compliance $C_{ic}$ is a strong function of ICP, $p_{ic}(t)$ 420.

Applicants modified the model in [20] so as to construct a computational model 400 that captures the pulsatile (as opposed to cycle-averaged or averaged) dynamics of the cerebrovascular system. In this manner, parameters and variables of computational model 400 now assume instantaneous values rather than averaged values, and averages based on running windows may be computed for the cerebrovascular pressures and flows, and may be used to update the cerebrovascular resistance $R_a$ and cerebrovascular compliance $C_a$ at every beat in the window. Applicants also modified the model in [20] so as to define an input flow q(t) to the model as a representative measurement of CBF, instead of flow through $R_a$ as defined in [20]. Note that in this disclosure cerebrovascular resistance is denoted $R_a$ or R, while cerebrovascular compliance is denoted $C_a$ or C.

With the limited availability of clinical measurements, it is not possible to reliably estimate all the model parameters in computational model 400. Moreover, all the parameters of model 400 do not need to be estimated—only those that are relevant to ICP $p_{ic}(t)$, cerebrovascular resistance $R_a$, and cerebrovascular compliance $C_a$. Therefore, Applicants performed a model reduction of the computational model FIG. 4A to obtain the computational model 450 shown in FIG. 4B.

To propose and construct computational model 450, Applicants made two main observations regarding computational model 400. First, a physiologically-inspired separation of time-scales is possible between the blood flow and the CSF flow dynamics, because the latter occur at a very slow rate (at least by two orders of magnitude), since the resistance of the CSF formation pathway is at least three orders of magnitude higher than the arterial-arteriolar resistance $R_a$. Therefore, the flow through this path is negligible compared to arterial flow over short time windows of a few beats. Similarly, the resistance of the CSF re-absorption or outflow channels is much higher than the resistance in the cerebrovascular blood vessels and can be assumed to be an open circuit. Second, one can ignore the relatively small intra-beat variability (about 8 mmHg) of ICP compared to that of ABP (about 50 mmHg). Therefore, when one estimates the incremental volume stored in the arterial compliance C over a fraction of a beat, the changes in transmural pressure can be assumed to be only due to changes in ABP (rather than ABP and ICP).

These observations may be stated in an alternate way: model 400 exhibits two time-scales which are significantly different, one being on the order of the length of a cardiac cycle or beat and the other being normally a couple of orders of magnitude longer. Since Applicants are interested in analyzing the model 400 at the time-scale of the beat interval, Applicants safely ignore the slow modes in model 400 to obtain model 450.

Figure 5:
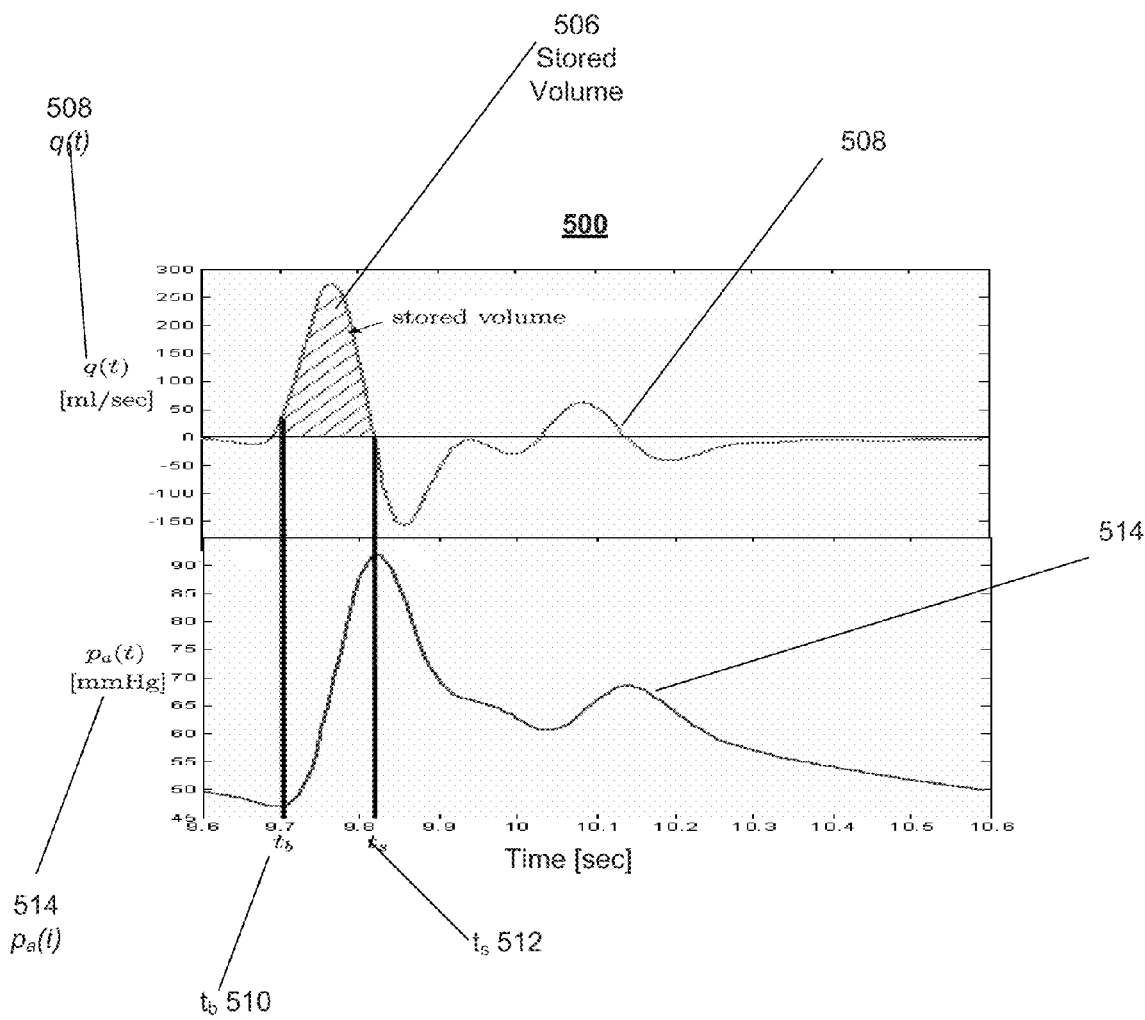
FIG. 5 illustrates representative CBF and ABP waveforms used to estimate cerebrovascular compliance, according to an illustrative embodiment.
Figure 6:
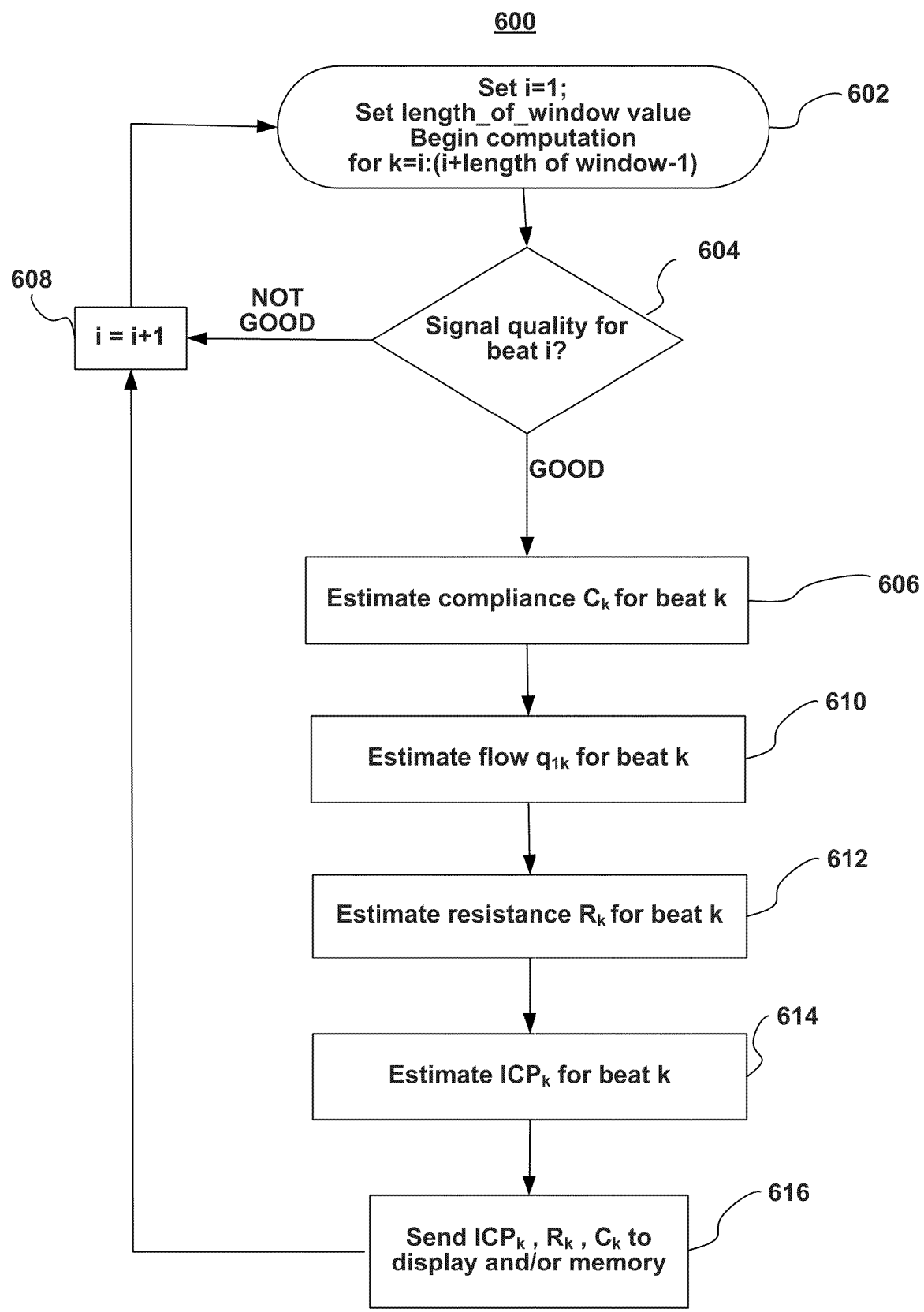
FIG. 6 is a process flow diagram of an estimation algorithm for estimating cerebrovascular parameters and variables, according to an illustrative embodiment.

The computational model 450 may be described by the following linear time-invariant differential equation, which forms the basis for the estimation algorithm described further in reference to FIGS. 5 and 6:

$$q(t) = C\left(\frac{dp_a(t)}{dt} - \frac{dp_{ic}(t)}{dt}\right) + \frac{1}{R}(p_a(t) - p_{ic}(t)), \quad (1)$$

Computational model 450 mimics the behavior of the larger model 400 reasonably well over time intervals that are on the order of a cardiac cycle or beat. Since cerebrovascular parameters vary slowly (via regulatory mechanisms), the coefficients in (1) are assumed to be constant over a beat period or over an estimation window comprising several consecutive beats. However, as the estimation window advances across the data, the estimates of the parameters in (1) capture the variation in these cerebrovascular variables. With computational model 450, only three unknown parameters, namely ICP 470 $p_{ic}(t)$, cerebrovascular resistance R, and cerebrovascular compliance C, need to be estimated using measurements of the ABP signal $p_a(t)$ and the CBF signal q(t). In some embodiments, CBFV may be used instead of, or in addition to, CBF. Note that in this disclosure cerebrovascular resistance is denoted $R_a$ or R, while cerebrovascular compliance is denoted $C_a$ or C. Note further that ICP 470 may be estimated as the pressure downstream of cerebrovascular resistance R, or as the pressure downstream of the cerebrovascular compliance C. Embodiments will now be described with respect to estimating ICP 470 downstream of the cerebrovascular resistance R. Computational model 450 is the basis for the estimation algorithms described in reference to FIGS. 5 and 6.

Estimation Algorithms for Computational Models

Using computational model 450 and the corresponding differential equation (1), Applicants estimate one or more of ICP 420 $p_{ic}(t)$, cerebrovascular resistance $R_a$, and cerebrovascular compliance $C_a$, using received measurements of the ABP signal $p_a(t)$ and the CBF signal q(t). Such an estimation algorithm may be implemented by configuring one or more of the processors in the processing unit 104 of FIG. 1 to perform the various steps of the estimation algorithm.

Two-Stage Estimation Algorithm

In some embodiments, given access to an ABP waveform $p_a(t)$ and a CBF waveform q(t) as received measurements, a two-stage estimation algorithm may be used to estimate model parameters for computational model 450 in FIG. 4B.

FIG. 5 illustrates representative cerebrovascular blood flow q(t) and arterial blood pressure $p_a(t)$ measurements used to estimate cerebrovascular compliance $C_a$ in the first stage of the two-stage estimation algorithm. In the second stage, cerebrovascular resistance $R_a$ and ICP $p_{ic}$ are estimated.

With continued reference to FIGS. 4B and 5, because sharp transitions in $p_a(t)$ 514 induce a large flow into the cerebrovascular compliance C, and because there is a comparatively negligible flow through the cerebrovascular resistance R during such transitions as they occur over short enough periods, the input flow q(t) 508 in model 450 in FIG. 4B can be attributed primarily to the cerebrovascular compliance during such sharp transitions:

$$q(t) \approx C_a \frac{dp_a(t)}{dt} \quad (2)$$

for $t_b < t < t_s$. Assuming $t_b$ (510) and $t_s$ (512) indicate the beginning and end of the sharp transition, respectively, in a particular beat of ABP waveform $p_a(t)$ (514), one can estimate $C_a$ by integrating (2) over the transition period to get stored volume (506), and divide it by the pressure differential between the beginning and end of the transition:

$$\hat{C}_a = \frac{\int_{t_b}^{t_s} q(t)dt}{p_a(t_s) - p_a(t_b)}. \quad (3)$$

This integration process is demonstrated graphically in FIG. 5. Someone skilled in the art will recognize that $t_b$ (510) and $t_s$ (512) need not be chosen to coincide with the arterial diastolic or systolic pressures, respectively, but may be chosen as other fiducial markers of rapid transitions in arterial blood pressure.

To cope with measurement noise in the received waveforms, Applicants have also proposed performing a least-squared error estimate for $C_a$ over N consecutive beats, or a window of size N, of the received measurements, assuming $C_a$ is approximately constant over the window. In general, N may be any suitable number of beats (e.g., 1, 2, 5, 10, 15, 21, 31, 61, etc., though odd numbers are sometimes more convenient than even). Re-arranging (3) and collecting N beats of $\Delta p_a(t)$ and $q(t)$ measurements in a vector gives the following expression:

$$[\Delta p_a[n], \Delta p_a[n+1], \ldots, \Delta p_a[n+N-1]]C_a \approx \qquad (4)$$
$$[Q[n], Q[n+1], \ldots, Q[n+N-1]],$$

where $$Q[n] = \int_{t_b[n]}^{t_s[n]} q(t)dt, \qquad (5)$$

and $$\Delta p_a[n] = p_a(t_s[n]) - p_a(t_b[n]), \qquad (6)$$

and $t_b[n]$ and $t_s[n]$ are appropriately chosen fiducial markers of sharp transitions in the $n^{th}$ blood pressure wavelet (cycle or beat). The estimate of $C_a$ thus obtained is:

$$\hat{C}_a = \frac{\sum_n \Delta p_a[n]Q[n]}{\sum_n (\Delta p_a[n])^2} \qquad (7)$$

This value $\hat{C}_a$ (may be attributed to the middle beat, i.e., the estimate is stored as $\hat{C}_a$ [n+(N−1)/2] for odd N, and is generally held constant over the corresponding beat period $T_n = t_b$ [n+1]−$t_b$[n]. Advantageously, this method of solution provides a smoother estimate of $C_a$ than that of (3).

Using the result of the estimation of $C_a$ as described above, and again ignoring ICP variations over the duration of a single beat or estimation window, one can assume the flow $q_1(t)$ through R is given by:

$$\hat{q}_1(t) = q(t) - \hat{C}_a \frac{dp_a(t)}{dt} \qquad (8)$$

Note that direct computation of the derivative involved above may accentuate noise in the received ABP measurements. Assuming that the resistance $R_a$ stays constant over the interval of a cardiac cycle or beat, ICP can be computed using $\hat{q}_1(t)$ as:

$$p_{ic}(t) = p_a(t) - R_a\hat{q}_1(t) \qquad (9)$$

Assuming further that ICP stays approximately constant within a beat, Applicants may estimate $R_a$ from (9) using $\hat{q}_1(t)$ and $p_a(t)$ evaluated at two or more time instants t. For example, by picking $t_1$ and $t_2$ within a beat, (8) yields $$\hat{R}_a = \frac{p_a(t_2) - p_a(t_1)}{\hat{q}_1(t_2) - \hat{q}_1(t_1)}. \qquad (10)$$

To reduce sensitivity to the noise in $\hat{q}_1(t)$, it is advantageous to pick $t_1$ and $t_2$ to lie near the maximum and minimum of the ABP waveform so that $$\frac{dp_a(t)}{dt} \approx 0$$

in (8). With this choice the estimate of $R_a$ is minimally-dependent on the estimate of $C_a$. Re-writing (9) in terms of beat-to-beat averages now gives the desired estimate for ICP $\bar{p}_{ic}$:

$$\hat{\bar{p}}_{ic} = \bar{p}_a - \hat{R}_a\bar{\hat{q}}_1, \qquad (11)$$

where $\bar{p}_a, \bar{p}_{ic}, \bar{\hat{q}}_1$ indicate the ABP, ICP and $\hat{q}_1(t)$ are averaged over a beat period.

To cope with error due to timing jitter in marking the discrete-time indices in (10), and to improve robustness against measurement noise, the equation may be solved for several consecutive beats using a least-squared error criterion, just as was done for the solution of (3) as described above. This method of solution of a least-squares equation advantageously provides smoother estimates of $R_a$, and thus ICP. In some embodiments, the estimation algorithm may involve employing a sliding window of N consecutive beats, computing the estimates as described above, and associating the estimated values of the parameters and variables to the time index of the middle beat of the chosen data window. For instance, to cope with measurement noise, Applicants propose averaging over a window of observed waveforms. Estimation over a few such collected points can then be set up as a least-squares solution to the system of equations:

$$[\delta q[n], \delta q[n+1], \ldots, \delta q[n+N-1]]R_a = [\delta p_a[n], \delta p_a[n+1], \ldots, \delta p_a[n+N-1]], \qquad (12)$$

where $$\delta x[n] = x(t_2[n]) - x(t_1[n]), \qquad (13)$$

where $x = q$ or $p_a$, and $t_1[n]$ and $t_2[n]$ are the time points chosen in the $n^{th}$ beat. Again, in one embodiment, the choices for $t_1$ and $t_2$ are the local minimum and maximum points within each beat where $$\frac{dp_a(t)}{dt} = 0.$$

Single-Stage Estimation Algorithm

In some embodiments, given access to an ABP waveform $p_a(t)$ and a CBF waveform $q(t)$ as received measurements, a one-stage or single-stage estimation algorithm may be used to estimate model parameters for computational model 450 in FIG. 4B. This approach involves applying a mod-function approach [32] to identify the model parameters of computational model 450 in FIG. 4B. By choosing a data segment of appropriate size, possibly a fraction of the cardiac beat duration, and integrating the evolution equation (1) of the reduced-order model over that data segment, with $p_{ic}(t)$ assumed to be constant, we obtain one equation for the three unknowns in the estimation problem: $C_a$, $R_a$ and ICP $p_{ic}$. By selecting several such segments, one may obtain a system of equations which can be solved for the three unknown parameters/variables by a least-squared error approach, for example. Someone skilled in the art will recognize that one can identify the desired parameters through different choices of data windows or by a different choice of optimization methods.

Timing Offset Correction

Since the ABP and CBF or CBFV measurements may be made at different anatomical sites, there may be an unknown timing offset between the pressure and flow waveforms. In some embodiments, this offset may be compensated for prior to application of any of the estimation algorithms described herein. For this purpose, the Applicants developed and implemented a routine that constructs a set of offset candidates and corresponding estimation results. All the candidate results may be displayed, or the algorithm may choose from among them according to some criterion, for instance to a minimal dispersion of ICP estimates, and to keep the estimates within a realistic range of values. The offset selection mechanism could also make use of the physiological relationships that exist between cerebral pressure and flow.

Process Flow Diagram for Two-Stage Estimation Algorithm

FIG. 6 is a process flow diagram of a two-stage estimation algorithm for estimating cerebrovascular parameters and variables of computational model 450 of FIG. 4, according to an illustrative embodiment. This process may be implemented on processing unit 104 of FIG. 1. The steps shown in FIG. 2 are only illustrative and in general may be performed in any order. In addition, some of the steps shown in FIG. 2 may be optional.

With continued reference to FIGS. 1, 4B, and 6, a window of pre-determined size length of window is selected, and a computation loop is initiated by setting the beat index variable i=1 (602). If the signal quality of beat i is sufficient for reliably obtaining the parameter and variable estimates (604), compliance $C_k$ for beat k is estimated as described above in relation to FIG. 5 (606). Flow $q_k$ for beat k is then estimated as described above in relation to FIG. 5 (610). Resistance $R_k$ for beat k (612), and $ICP_k$ for beat k (614) are also estimated. The computed estimates $R_k$, $C_k$, and $ICP_k$ are also then displayed (e.g., on display 108) or stored in memory e.g., memory 106 of FIG. 1 (616). This process is repeated until estimates of $R_k$, $C_k$, and $ICP_k$ are obtained for all k beats in the window (608). If the signal quality of the received measurements for beat i are not sufficient for reliably obtaining the parameter and variable estimates (604), the beat is skipped and not used in the computation of estimates $R_k$, $C_k$, and $ICP_k$.

The estimation algorithm described in reference to FIGS. 5 and 6 allows for continuous beat-by-beat estimates of the cerebrovascular compliance and cerebrovascular resistance. From these two estimates, we can observe the response of the cerebral vasculature during the time interval of a drop/rise in CBFV caused by variations in ABP and/or ICP. This approach exploits the availability of the ICP estimate, which can be used to obtain an estimate of CPP. For instance, one can characterize the status of pressure autoregulation by analyzing the dynamic trends in resistance and compliance at such episodes of sudden variations in CPP, checking whether these parameters adjust themselves to keep the desired CBF steady, and the time-constants of these variations. Variations in CPP may occur naturally or may be externally induced. An assessment of cerebrovascular autoregulation in this manner aids in characterizing the injury and recovery process, for example, in patients of head trauma and stroke.

Estimates of ICP Obtained Using the Estimation Algorithm(s)

Applicants have applied their estimation algorithm(s) described above to both simulated (described in [16]) and actual patient data in which the desired measurements (e.g., ABP and CBFV) and actual (i.e., invasively obtained) ICP were available. In the results obtained and illustrated in FIGS. 7-9, Applicants applied the algorithms described above to estimate ICP, and compared the estimates of ICP to the actual ICP measurements.

Applicants thank Dr. Marek Czosnyka of Addenbrooke's Hospital, Cambridge, U.K., for his generosity in making the patient data used for illustration in this patent application available to the Applicants. The patient database provided by Dr. Czosnyka includes clinical data records of sedated/comatose patients suffering from severe TBI. Each patient record includes continuous recordings of CBFV via unilateral transcranial Doppler, ABP via an intra-arterial radial artery catheter or a Finapres device, and ICP via a parenchymal probe. Each patient record contains measurements obtained over a continuous stretch of time that varies between 15 minutes and four hours across the patients. All waveforms are sampled at the same sampling frequency for a given patient, but varying across the patient records from 20 Hz to 70 Hz.

FIG. 7 illustrates comparisons of estimates of ICP with actual ICP measurements for two patients from the above-described patient database. The left panel 700 illustrates data for a patient with a case of intracranial hypertension (IH) where ICP 710 increases from 60 mmHg to 120 mmHg over a period of one hour. The ICP estimate 720 produced by applying Applicants' method to the available CBFV and ABP measurements falls close to the actual measurement and tracks the variations in actual ICP 710 very well. The right panel 750 shows a case of the so-called plateau-wave phenomenon, where ICP suddenly increases from its base level and stays elevated for at least a few minutes before dropping back to its previous level. The ICP estimate 770 produced by applying Applicants' method to the available CBFV and ABP measurements tracks the transients in actual ICP 760 quite precisely.

Assessment of Cerebrovascular Autoregulation

FIG. 8 illustrates the use of cerebrovascular resistance and compliance estimates along with CPP estimates to obtain an assessment of cerebrovascular autoregulation for the second patient of panel 750 in FIG. 7. Graph 800 of FIG. 8 focuses on the first plateau-wave from 750 in FIG. 7 where ICP increases, causing CPP 810 and thus CBFV 820 to decrease near time t=32 minutes. The bottom panel 830 shows the corresponding estimate of cerebrovascular resistance. Applicants note that cerebrovascular resistance drops to about half of its initial value, leading to a CBF restored to its base level before CPP returns to its base level near t=42 minutes. An opposite trend is observed in cerebrovascular resistance when ICP falls below from its plateau, leading to an increase in CPP near t=45 minutes. This dynamic behavior of cerebrovascular resistance can be inferred as being an assessment of the cerebrovascular autoregulation as being "intact" or "functional".

Discussion

Applicants note that the estimation performance of the estimates in FIGS. 7-8 relies on a sufficient signal quality for the received measurements. Signal quality in turn depends on noise and other artifact in the received measurements or waveforms as well as the sampling rate of the data acquisition system or sensing device. Noise in the measurements degrades the estimation performance, e.g., it makes the approximation of the derivative in (7) poorer. Appropriate pre-processing may be applied to improve the signal quality as described above.

Any further errors in the ICP estimates shown in FIGS. 7-8 may be attributed to the fact that the ABP measurements were obtained from a radial artery catheter or finger Finapres device, instead of a sensor located at the site of flow measurement (cerebral artery). This results in possible discrepancies in the measured pressure amplitude and timing compared to the actual cerebral pressure amplitude and timing. In one embodiment, the Applicants' algorithm includes a routine for adjustment of the timing offset between the acquired ABP and CBF or CBFV waveforms to compensate for the discrepancy.

Since Applicants employ time domain analysis of the ABP and CBFV waveforms, incorporating mechanisms to extract beat morphology/intra-beat features and their variations, the sampling rate for the received measurements may have an impact on performance. This sampling rate determines, for example, the timing jitter in the discrete-time indices for beat-onset detection and for marking intra-beat indices by the algorithm; a low sampling rate adds more noise to these marker locations and introduces both bias and dispersion in estimates. The results presented in FIGS. 7-8 above were obtained for waveforms sampled between 30 Hz and 70 Hz. The estimation performance is expected to improve by increasing the sampling frequency to 100 Hz and above. Furthermore, dispersion in the estimates may be controlled by some algorithm choices, such as the number of consecutive beats (or window length) used to set up the least-squares equation-error formulation for a robust estimate of the parameters. A larger window may serve to average out the noise better but can degrade tracking of the transients. A window length of 15 beats was used in the results reported above.

The invention may be embodied in other specific forms without departing from the spirit or essential characteristics thereof. For instance, the methods and systems described herein may be employed in any device, method, or system, without limitation. The foregoing embodiments are therefore to be considered in all respects illustrative, rather than limiting of the invention. For instance, while embodiments have been described with relation to the estimation of one or more cerebrovascular parameters or variables using a computational model, it is to be understood that the systems, devices and methods discussed herein are applicable to medical applications in which the other physiological parameters or variables are estimated using computational models similar to those described herein.

Reference Listing

[1] American Heart Association. Heart disease and stroke statistics. *Circ*, 119(3): E21-181, 2009.

[2] Institute of Medicine. *Long-Term Consequences of Traumatic Brain Injury, volume 7 of Gulf War and Health*. National Academy of Sciences, Washington, D.C., 2009.

[3] C. W. Hoge, D. McGurk, J. L. Thomas, C. C. Cox, A. L. Engel, and C. A. Castro. Mild traumatic brain injury in U.S. soldiers returning from Iraq. *N Engl J Med*, 358(5):453-463, 2008.

[4] D National Academy of Engineering and Institute of Medicine. *System Engineering to Improve Traumatic Brain Injury Care in the Military Health System*, The National Academy Press, Washington, D.C., 2009.

[5] A. Saljo, B. Svensson, M. Mayorga, A. Hamberger and H. Bolouri. Low-level blasts raise intracranial pressure and impair cognitive function in rats. *J Neurotrauma*, 26:1345-1352, 2009.

[6] J. D. Miller, D. P. Becker, J. D. Ward, H. G. Sullivan, W. E. Adams, and M. J. Rosner. Significance of intracranial hypertension in severe head injury. *J Neurosurg*, 47:503-516, 1977.

[7] E. R. Kandel, J. H. Schwartz and T. M. Jessell, *Principles of Neural Science*, New York: McGraw Hill, 2000.

[8] The Brain Trauma Foundation. Guidelines for the management of severe traumatic brain injury, 3rd edition. *J Neurotrauma*, 24:S1-S106, 2007.

[9] A. Ragauskas et al. Non-invasive technology for monitoring of intracranial volumetric pulse waves and trends, *Electronic and Electrical Engineering, Medicine Technology*, No. 6(86): 2008.

[10] Non-invasive method of measuring cerebral spinal fluid pressure, U.S. Pat. No. 6,129,682.

[11] Non-invasive method and apparatus for monitoring intracranial pressure, U.S. Pat. No. 6,589,189.

[12] A Reid, R J Marchbanks, D E Bateman, A M Martin, A P Brightwell, and J D Pickard. Mean intracranial pressure monitoring by a non-invasive audiological technique: a pilot study. *J Neurol Neurosurg Psychiatry*. 52(5): 610-612, 1989.

[13] P. B. Raksin, N. Alperin, A. Sivaramakrishnan, S. Surapaneni, and T. Lictor. Noninvasive intracranial compliance and pressure based on dynamic magnetic resonance imaging of blood flow and cerebrospinal fluid flow: review of principles, implementation, and other noninvasive approaches. *Neurosurg Rev*. 14(4):e4, 2003.

[14] W. Wakeland, R. Agbeko, K. Vinecore, M. Peters, and B. Goldstein. Assessing the prediction potential of an in silica computer model of intracranial pressure dynamics. *Crit Care Med*. 37(3):1079-1089, 2009.

[15] B. Schmidt, M. Czosnyka, A. Raabe, H. Yahya, J. J. Schwarze, D. Sackerer, D. Sander and J. Klingelhöfer. Adaptive noninvasive assessment of intracranial pressure and cerebral autoregulation. *Stroke*. 34:84-89, 2003.

[16] F. M. Kashif, T. Heldt and G. C. Verghese. Model-based estimation of intracranial pressure and cerebrovascular autoregulation. *Computers in Cardiology*, 35: 369-372, 2008.

[17] M. Ursino and C. A. Lodi. A mathematical study of human intracranial hydrodynamics, part 1—the cerebrospinal fluid pulse pressure. *Ann of Biomedical Eng*, 16(4):379-401, 1988.

[18] M. Ursino and C. A. Lodi. A mathematical study of human intracranial hydrodynamics, part 2—simulation of clinical tests. *Ann of Biomedical Eng*, 16(4):403-416, 1988.

[19] M. Ursino and C. A. Lodi. Interaction among autoregulation, $CO_2$ reactivity, and intracranial pressure: a mathematical model. *Am J of Physiology—Heart and Circulatory Physiology*, 274:1715-1728, 1998.

[20] M. Ursino and C. A. Lodi. A simple mathematical model of the interaction between intracranial pressure and cerebral hemodynamics. *J App Physiology*, 82:1256-1269, 1997.

[21] A. Marmarou, K. Shulman, and R. M. Rosende. A nonlinear analysis of the cerebrospinal fluid system and intracranial pressure dynamics. *J Neurosurg*, 48:332-344, 1978.

[22] W. Wakeland and B. Goldstein. A review of physiological simulation models of intracranial pressure dynamics. *Comput Biol Med*, 38:1024-41, 2008.

[23] S. A. Stevens, J. Stimpson, W. D. Lakin, N. J. Thakore and P. L. Penar. A model for idiopathic intracranial hypertension and associated pathological ICP waveforms. *IEEE Trans on Biomedical Eng*, 55(2): 388-398, 2008.

[24] N. Lundberg. Continuous recording and control of ventricular fluid pressure in neurosurgical practice. *Acta Psychiatrica et Neurologica Scandinavica*, 36(Supplement 149): 1-193, 1960.

[25] M. Hayashi, Y. Handa, H. Kobayashi, H. Kawano, H. Ishii and S. Hirose. Plateau-wave phenomenon (I). *Brain*, 114:2681-2691, 1991.

[26] M. Hayashi, H. Kobayashi Y. Handa, H. Kawano, S. Hirose, and H. Ishii. Plateau-wave phenomenon (II). *Brain*, 114:2693-2699, 1991.

[27] F. Bono et al. Bilateral transverse sinus stenosis predicts 11H without papilledema in patients with migraine. *Neurology*, 67: 419-423, 2006.

[28] M. T. Torbey, R. G. Geocadin, A. Y. Razumovsky, D. Rigamonti and M. A. Williams. Utility of CSF pressure monitoring to identify idiopathic intracranial hypertension without papilledema in patients with chronic daily headache. *Cephalalgia*, 24:495-502, 2003.

[29] M. De Bor and F. J. Walther. Cerebral blood flow velocity regulation in preterm infants. *Biol Neonate*, 59:329-335, 1991.

[30] A. J. du Plessis. Cerebrovascular injury in premature infants: current understanding and challenges for future prevention. *Clin Perionatol*, 35(4):609-41, 2008.

[31] Frederic H. Martini, Michael J. Timmons, and Bob Tallitsch. *Human Anatomy*. Benjamin Cummings, Pearson, 6th edition, 2009.

[32] G. P. Rao and H. Unbehauen. Identification of continuous-time systems. *IEEE Proc.—Control Theory Applications*, 53(2):185-220, 2006.

What is claimed is:

1. A method for computing a series of estimates of a selected cerebrovascular property comprising at least one of a cerebrovascular resistance, an intracranial pressure, and a cerebrovascular compliance, comprising:
receiving, at a processor, a series of arterial blood pressure measurements of a particular patient;
receiving, at the processor, a series of cerebrovascular flow measurements of the particular patient, the cerebrovascular flow measurements comprising at least one of cerebral blood flow measurements and cerebral blood flow velocity measurements; and
computing, with the processor, a series of estimates of the selected cerebrovascular property based at least in part on a corresponding series of estimates of elements of a computational model using the corresponding received measurements, the computational model representing predicted relationships among computational model elements corresponding to physiological properties, including a cerebrovascular resistance element, a cerebrovascular compliance element, an intracranial pressure element, an arterial blood pressure element and a cerebrovascular flow element;
wherein computing each estimate in the series of estimates of the selected cerebrovascular property comprises:
selecting values for at least one of the elements of the computational model to minimize an error criterion between the received measurements and predictions, by the computational model, of the elements corresponding to the received measurements; and
identifying the selected value of the element corresponding to the selected cerebrovascular property as the estimate of the selected cerebrovascular property.

2. The method of claim 1, further comprising computing, with the processor, an estimate of an assessment of cerebrovascular autoregulation.

3. The method of claim 1, further comprising computing, with the processor, an estimate of a blood flow through the cerebrovascular resistance using an estimate of the cerebrovascular compliance.

4. The method of claim 1, wherein at least one of the elements is computed at least once per cardiac cycle.

5. The method of claim 1, wherein at least one of the elements is estimated using a data window of a pre-specified size.

6. The method of claim 1, wherein computing estimates of the elements comprises using a two-stage algorithm.

7. The method of claim 6, wherein computing estimates of the elements comprises computing estimates of a cerebrovascular compliance in a first stage of the two-stage algorithm.

8. The method of claim 6, wherein computing estimates of the elements comprises computing estimates of at least one of a cerebrovascular resistance and the intracranial pressure in a second stage of a two-stage algorithm.

9. The method of claim 1, wherein the error criterion is least squared-error.

10. The method of claim 1, wherein the processor does not receive, prior to computing at least one estimate in the series of estimates of the selected cerebrovascular property, patient-specific invasive intracranial pressure training data or population-specific invasive intracranial pressure training data.

11. The method of claim 1, wherein the estimate of the selected cerebrovascular property is a relative estimate.

12. A device for computing a series of estimates of a selected cerebrovascular property comprising at least one of a cerebrovascular compliance, a cerebrovascular resistance, and an intracranial pressure, the device including:
a processor, the processor configured to:
receive a series of arterial blood pressure measurements of a particular patient;
receive a series of cerebrovascular flow measurements of the particular patient, the cerebrovascular flow measurements comprising at least one of cerebral blood flow measurements and cerebral blood flow velocity measurements;
compute a series of estimates of the selected cerebrovascular property based at least in part on a corresponding series of estimates of elements of a computational model using the corresponding received measurements, the computational model representing predicted relationships among computational model elements corresponding to physiological properties, including a cerebrovascular resistance element, a cerebrovascular compliance element, an intracranial pressure element, an arterial blood pressure element and a cerebrovascular flow element,
wherein computing each estimate in the series of estimates of the selected cerebrovascular property comprises:
selecting values for at least one of the elements of the computational model to minimize an error criterion between the received measurements and predictions, by the computational model, of the elements corresponding to the received measurements, and
identifying the selected value of the element corresponding to the selected cerebrovascular property as the estimate of the selected cerebrovascular property;
a memory in communication with the processor for storing at least one of the received measurements and the computed estimate of the selected cerebrovascular property; and
a display in communication with the processor for displaying the estimate of the selected cerebrovascular property.

13. The device of claim 12, further comprising:
a sensing device in communication with the processor for sensing the arterial blood pressure measurements.

14. The device of claim 13, wherein the sensing device includes at least one of an arterial catheter, a tonometry sensor, a sphygmomanometer sensor, and a photoplethysmography sensor.

15. The device of claim 12, further comprising:
a sensing device in communication with the processor for sensing the cerebrovascular flow measurements.

16. The device of claim 15, wherein the sensing device includes an ultrasound sensor.

17. The device of claim 12, further comprising a signal quality processor in communication with the processor configured to assess the quality of the received measurements.

18. The device of claim 17, wherein the signal quality processor is configured to remove unwanted portions of the received measurements.

19. The device of claim 18, wherein the unwanted portions include noise and artifact.

20. The device of claim 12, further comprising a smoothing processor configured to filter the computed estimate of the selected cerebrovascular property.

21. The device of claim 20, wherein the smoothing processor is configured to filter the computed estimate of the selected cerebrovascular property using a median filter.

22. The device of claim 12, further comprising an extraction processor for extracting intra-beat features of the received measurements.

23. The device of claim 12, wherein at least one of the elements is computed at least once per cardiac cycle.

24. The device of claim 12, wherein the processor estimates at least one of the elements using a data window of a pre-specified size.

25. The device of claim 12, wherein the processor computes estimates of the elements using a two-stage algorithm.

26. The device of claim 25, wherein the processor computes an estimate of a cerebrovascular compliance in a first stage of the two-stage algorithm.

27. The device of claim 25, wherein the processor computes an estimate of at least one of a cerebrovascular resistance and an intracranial pressure in a second stage of the two-stage algorithm.

28. The device of claim 12, wherein the processor does not receive, prior to computing at least one estimate in the series of estimates of the selected cerebrovascular property, patient-specific invasive intracranial pressure training data or population-specific invasive intracranial pressure training data.

29. The device of claim 12, wherein the estimate of the selected cerebrovascular property is a relative estimate.

30. The device of claim 12, wherein the processor further computes an estimate of an assessment of cerebrovascular autoregulation.

* * * * *